United States Patent

Morin et al.

[11] Patent Number: 5,173,133
[45] Date of Patent: Dec. 22, 1992

[54] METHOD FOR ANNEALING STAPLER ANVILS

[75] Inventors: Donald A. Morin, Litchfield, Conn.; Bartolo Sciano, Jr., Glen Rock, N.J.

[73] Assignee: United States Surgical Corporation, Norwalk, Conn.

[21] Appl. No.: 734,596

[22] Filed: Jul. 23, 1991

[51] Int. Cl.$^5$ .............................................. C21D 9/00
[52] U.S. Cl. ................... 148/567; 148/570; 148/590; 76/101.1; 219/10.41; 219/10.43; 227/175; 227/180; 606/220
[58] Field of Search ............... 148/154, 134, 135, 150; 227/175, 180; 606/220; 76/101.1; 219/10.41, 10.43

[56] References Cited

U.S. PATENT DOCUMENTS

| | | | |
|---|---|---|---|
| 3,079,606 | 3/1963 | Bobrov et al. | 227/76 |
| 3,490,675 | 1/1970 | Green et al. | 227/19 |
| 3,499,591 | 3/1970 | Green | 227/76 |
| 5,058,457 | 10/1991 | Deroulou et al. | 76/101.1 |

OTHER PUBLICATIONS

Mark's Standard Handbook for Mechanical Engineers, Ninth Ed., pp. 7-63 (1987).
Application of Electronic Induction Heating Equipment, dated 1956.

*Primary Examiner*—R. Dean
*Assistant Examiner*—Sikyin Ip
*Attorney, Agent, or Firm*—Thomas R. Bremer; Peter G. Dilworth; Rocco S. Barrese

[57] ABSTRACT

An anvil member for use in a surgical stapler is annealed by localized heating, preferably induction heating. A shaped shielding means is used to cradle the anvil so as to expose the staple crimping portion of the anvil. The heating is performed so as to anneal only the delimited staple crimping portion of the anvil. All other portions of the anvil are either shielded by the cradle or are out of the heating range.

21 Claims, 3 Drawing Sheets

METHOD FOR ANNEALING STAPLER ANVILS

BACKGROUND OF THE INVENTION

1. Field of the Invention

This invention relates to a method and apparatus for annealing the anvil members of surgical staplers, and more particularly to a method and apparatus for induction heating a specified portion of an anvil member.

2. Background of the Invention

Surgical stapling instruments are well known in the art. For example, U.S. Pat. Nos. 3,499,591; 3,490,675; and 3,079,606, all of which are incorporated by reference, describe surgical stapling instruments for applying multiple rows of metal staples sequentially to body tissue.

Typically, such instruments employ a metal anvil member to form or crimp the staples. The anvil member possesses an upper surface with staple crimping depression, or "pockets." When the staples are driven into the anvil the legs of the staple enter the pockets and are crimped, thereby securing the body tissue.

The anvil member is generally fabricated from a surgically acceptable strong metal alloy such as stainless steel. Bending forces develop during the operation of the instrument. Deflection of the anvil member under these bending force can lead to misalignment of the staples and pockets and subsequent jamming or failure to close all of the staples. The bending moment of the anvil increases in proportion to the length of the rows of staples to be applied. Hence, the anvil member, especially for instruments which apply relatively long rows of staples (e.g. with 80 mm. staple lines), must be very stiff.

Series 300 stainless steel has been used to fabricate the anvil. Formation of the anvil member by cold working a stainless steel sheet inherently hardens the steel to sufficient stiffness. Manufacture of the anvil member also involves creating the pockets by a "coining" process. When hardened steel is coined, the coining tool, a die which punches the depressions into the anvil, has a shortened life. Typically, the coining tool life for a cold worked steel anvil is about 100 punches. Consequently, it is advantageous in one respect to soften the anvil to increase the working life of the coining tool. Annealing is a well known method for softening steel. However, since annealing reduces the stiffness of the anvil it increases the tendency of the anvil to deflect in use. The problem, then, is to achieve extended coining tool life without weakening the anvil.

SUMMARY OF THE INVENTION

The aforementioned problem can be alleviated by localized annealing of the staple crimping surface of the anvil while leaving the remainder of the anvil unannealed. Presented herein is a method and apparatus for localized annealing of a delimited portion of an anvil, i.e. the staple crimping upper surface, while preventing the non-delimited portion from being annealed. The method includes the use of localized heating, preferably induction heating. The anvil is first placing the anvil in a cradle fabricated from a thermally and electrically conductive material such as copper. The cradle has a slot configured and dimensioned so as to receive the anvil such that a first part of the exterior surface of the anvil is in thermally and electrically conductive contact with the interior surface of the slot and a second part of the anvil is exposed. The cradle is positioned in proximity to the heater such that only the delimited portion of the exposed part of the anvil is within the heating range of said heating means. The heater is operated such that the delimited exposed portion of the anvil is heated to an annealing temperature, the anvil temperature being monitored, for example by optical pyrometry, to determine when the annealing temperature has been reached, after which the heating operation is terminated.

DETAILED DESCRIPTION OF PREFERRED EMBODIMENTS

Figure 1:
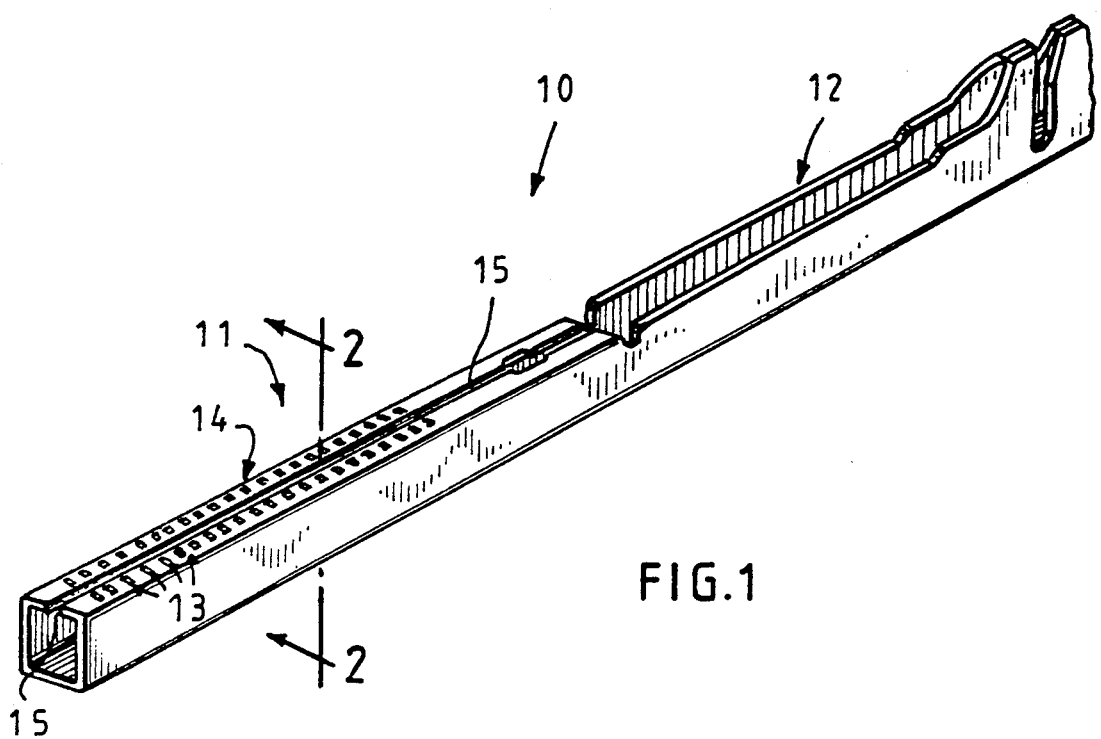
FIG. 1 is a perspective view of an anvil member.
Figure 2:
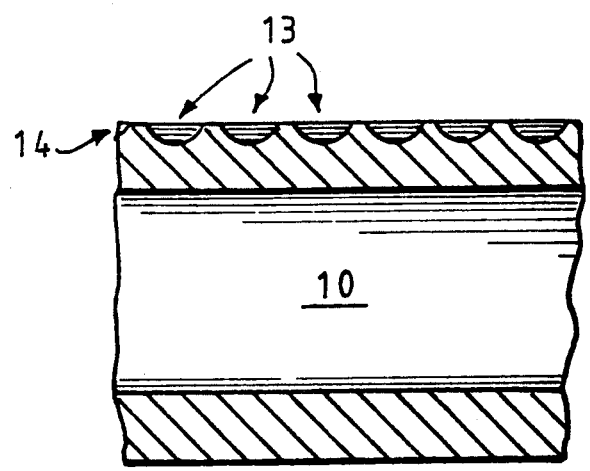
FIG. 2 is a sectional view of the anvil showing the staple crimping depressions or pockets.

FIGS. 1 and 2 illustrate an anvil member of the type commonly used in surgical stapling instruments. Anvil 10 is an elongated member having a distal portion 11 with an upper staple forming surface 14 and a proximal portion 12. The staple forming upper surface 14 includes a plurality of staple crimping depressions or pockets 13. A knife slot 15 extends lengthwise along the upper surface 14 to permit longitudinal movement of a tissue cutting knife blade (not shown).

Anvil member 10 is preferably fabricated from a sheet of stainless steel alloy, such as Series 300 stainless steel. The sheet steel is cold worked to form it generally into the configuration as shown in FIG. 1.

As explained above, cold working hardens the steel, which is desirable to prevent deflection during use of the stapler. Nevertheless, it is also desirable that the anvil be softened by annealing in order to extend the useful life of the coining tool. This is accomplished by localized annealing of only the upper surface 14 by induction heating. Preferably, the depth of annealing is from one to two thicknesses of the metal, and optimally about 1.5 times the thickness of the sheet metal.

Induction heating is a method of heating conductive materials by subjecting them to a powerful alternating magnetic field. Resistance to eddy currents induced by the alternating magnetic field generates heat internally in the workpiece. The power dissipated as heat in the workpiece is proportional to the resistivity of the workpiece and the square of the current flowing therein.

The induction heater generally comprises a source of alternating electric current, and an induction coil or load coil, usually a water cooled copper tube, which generates the magnetic field. The load coil may be thought of as acting as the primary coil of a transformer. No physical contact is made between the workpiece and the load coil.

Induction heating provides versatility with respect to localization of the heated area. Several factors influence the heating depth and pattern: frequency, power, power density, heating time, load coil shape, and workpiece geometry, electrical, magnetic and thermal properties. These factors influence one another. A brief review of these factors follows.

Conventional induction heaters may be operated at frequencies ranging from 60 Hz line frequency to above 40 MHz. A frequency of 450 kHz is useful for many metal treating applications. Higher frequencies (e.g. 500 kHz to above 1 MHz) are used when it is desired to localize the heating to the surface of the workpiece. Lower frequencies (e.g. 60 Hz to 10 kHz) permit penetration of the heating zone. The proper operating frequency also depends upon the geometry of the workpiece (a higher frequency is more efficient for a smaller diameter workpiece) and upon the resistivity of the workpiece (highly resistive materials such as semiconductors and nonconductors require megahertz frequencies for direct heating by induction).

When only surface heating is desired it is advantageous to operate at higher power levels and shorter heating times. Lower power levels and longer heating times permit thermal conduction of heat from the surface to the interior of the workpiece.

The shape of the magnetic field, and therefore the heating pattern, is determined by the shape of the load coil. Load coils can be helical shaped, flat spirals, elongated, squared, conical, etc. The optimum choice depends on the particular application and shape of the workpiece.

An important goal of the present invention is to limit the heated area of the anvil 10 substantially to the staple crimping upper surface 14. Accordingly, a special fixture, illustrated herein in FIGS. 3 to 5, was developed to cradle the anvil during the annealing process. The cradle 20 acts as a heat sink to prevent induction heating of the proximal portion 12, and the sides and bottom of the anvil member.

Figure 3:
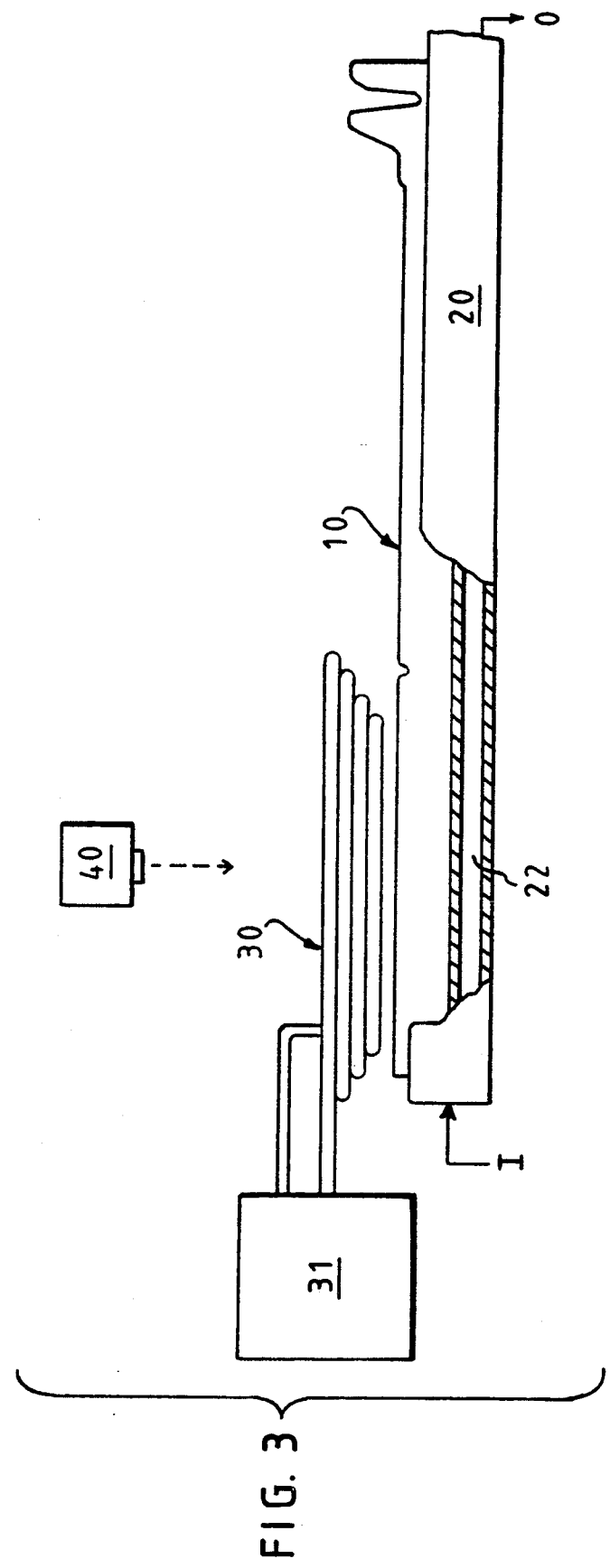
FIG. 3 is a side elevational view of the apparatus of the present invention showing means for localized induction heating of the anvil.
Figure 4:
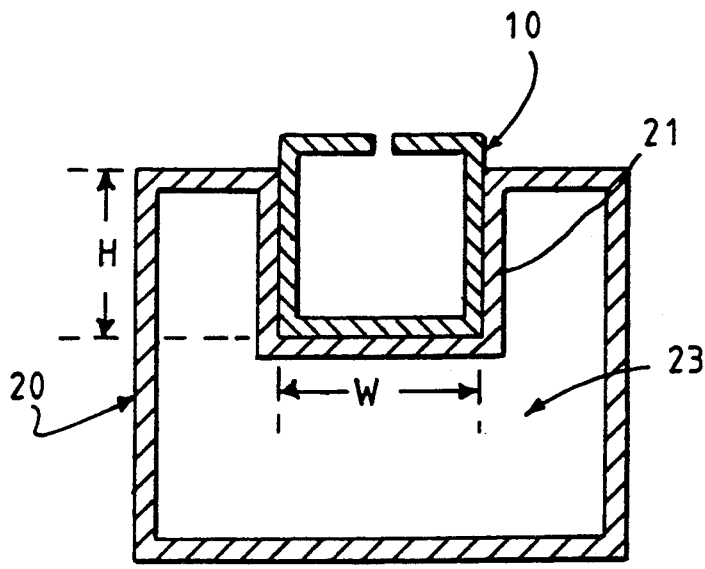
FIGS. 4 and 5 are cross sectional views of alternative embodiments of the shaped anvil cradle.
Figure 5:
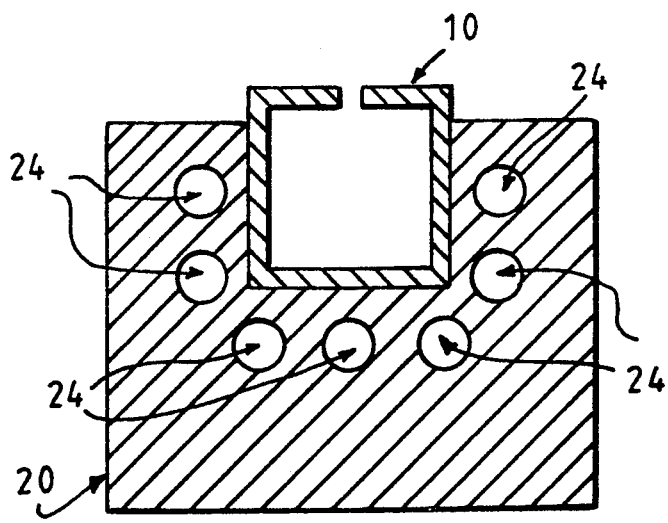

In accordance with the method of the present invention a formed but precoined anvil member 10 is positioned in a cradle or heatsink 20, as illustrated in FIG. 3. The cradle 20 comprises an elongated member, preferably fabricated from copper, with a longitudinal slot 21 having such slot width W so as to receive anvil member 10 with thermally conductive contact between the bottom and the outer walls of the anvil member 10 and the bottom and the inner walls of the slot 21. The height H of slot 21 is such as to allow the anvil to extend about 1/16″±1/32″ above the top of the cradle 20. Typically, the width W of the slot 21 is about 0.360 inches and the height H of slot 21 is about 0.30 inches. Cradle 20 is cooled by water (or other other coolant) flowing therethrough. The flow rate of the coolant is sufficient to keep the non-delimited portion of the anvil below the annealing temperature. FIG. 3 diagrammatically illustrates the coolant input I and output O, which may be accomplished by anyone with skill in the art. An interior passageway 22 in the cradle permits the flow through of coolant. FIG. 4 illustrates a cross section of the cradle wherein the interior passageway is a chamber 23. Alternatively, the cradle 20 may be constructed from a solid block of copper with internal coolant passageways 24 drilled therethrough in the form of cylindrical channels as shown in FIG. 5.

The cradle 20 is then positioned below the load coil 30 of an induction heater so as to leave a gap of from about 0.020 inches to about 0.030 inches between the load coil 30 and the upper surface 14 of the anvil. The shape of load coil 30 includes a series of elongated loops, the lowest loop conforming as closely as possible to the shape of the area of the anvil to be annealed, as shown in FIG. 3. This shape directs the heating energy to a localized area on the anvil surface. A coolant flows through load coil 30 to prevent meltdown. During operation, the coil may have to be fixtured to prevent movement. The range of operating conditions for the power supply are shown below in Table 1. An induction heater suitable for the present invention is available from Vacuum Tube Industries of Brockton, Mass.

TABLE 1

|  | Broad Range | Preferred |
| --- | --- | --- |
| Operating frequency, | 300 kHz to 450 kHz | 400 kHz to 440 kHz |
| Voltage | 200 V to 440 V | — |
| Power | 2.5 kW to 7.5 kW | 5 kW to 7.5 kW |
| Heating time | 10 sec. to 60 sec. | 20 sec. to 30 sec. |

The anvil 10 is heated such that the upper surface 14 reaches a temperature of from about 1900° F. to about 2000° F., and preferably from about 1925° F. to about 1975° F. The temperature can be measured by optical pyrometry. Referring to FIG. 3, the optical pyrometer 40 is positioned so as to face downward and take readings of the anvil surface through the center of coil 30. An optical pyrometer suitable for use in the present invention is available from PAR Associates, Inc. of Hohokus, N.J. 07423 under model name: RAYTEK THERMALERT 5S5XHTCF1.

The heating time to raise the anvil surface temperature from ambient to 1900° F. can be from about 20 seconds to 30 seconds. It is preferably not to hold the anvil at the annealing temperature for an extended period of time. Once the annealing temperature has been reached the anvil can be quickly cooled to sub-annealing temperature. A suitable procedure employs a water jacketed steel plate to cool the anvil to 900° F. in from about 45 seconds to about 55 seconds, after which the anvil may be allowed to cool to ambient temperature in about 60 to 90 seconds. Anvils annealed by the above method have increased the coining tool life from about 100 punches for an unannealed anvil up to about 2,500 punches, which represents a dramatic improvement in tool life and a corresponding reduction in down time and replacement costs. No substantial decrease in the anvil strength is observed.

What is claimed is:

1. A method for annealing a delimited portion of an anvil member for use in a surgical stapler said method comprising:
   a) providing a means for heating;
   b) placing said anvil member in cradle means, said cradle means comprising a member fabricated from a thermally conductive material and possessing means configured and dimensioned to receive said anvil such that a first part of the exterior surface of the anvil is in thermally conductive contact with the interior surface of the receiving means and a second part of the exterior surface of the anvil is exposed;
   c) positioning said cradle in proximity to said heating means such that the delimited portion of the second part of the exterior surface of the anvil member is within the heating range of said heating means; and
   d) operating said heating means such that the delimited exposed portion of the anvil member is heated to an annealing temperature.

2. The method of claim 1, wherein said heating means comprises an induction heating means.

3. The method of claim 2, wherein said induction heating means includes a load coil for providing an alternating magnetic field in response to the application of an alternating electric current applied thereto.

4. The method of claim 3, wherein said load coil is configured and dimensioned to direct heating energy to the exposed surface of the anvil.

5. The method of claim 3, wherein said alternating electric current is characterized by a frequency of from about 300 kHz to about 450 kHz, a voltage of from about 200 V to about 440 V, and a power of from about 2.5 kW to about 7.5 kW.

6. The method of claim 3, wherein said alternating electric current is characterized by a frequency of from about 400 kHz to about 440 kHz, a voltage of from about 200 V to about 440 V, and a power of from about 5 kW to about 7.5 kW.

7. The method of claim 3, wherein said alternating current is applied for a duration of from about 10 seconds to about 60 seconds.

8. The method of claim 3, wherein said alternating current is applied for a duration of from about 20 seconds to about 30 seconds.

9. The method of claim 1, wherein said anvil member is fabricated from a stainless steel alloy.

10. The method of claim 9, wherein said stainless steel alloy is Series 300 stainless steel.

11. The method of claim 1, wherein said cradle is fabricated from metal.

12. The method of claim 11, wherein said metal is copper.

13. The method of claim 1, wherein said annealing temperature is from about 1925° F. to about 1975° F.

14. The method of claim 1, wherein the anvil is cooled after the annealing temperature has been reached.

15. The method of claim 1, wherein said cradle possesses interior means extending longitudinally therethrough for the passage of a fluid coolant material, and said method further comprising the step of passing said coolant material through said interior passage means of the cradle.

16. The method of claim 15, wherein said coolant material is water.

17. The method of claim 15, wherein said interior passage means comprises a chamber.

18. The method of claim 15, wherein said interior passage means comprises at least one cylindrical channel.

19. The method of claim 1, further comprising monitoring the temperature of the delimited portion of the anvil member to determine when said delimited portion of the anvil member has reached said annealing temperature.

20. The method of claim 19, wherein said monitoring is accomplished by means of optical pyrometry.

21. A method for annealing a delimited portion of an anvil member for use in a surgical stapler, said method comprising:
   a) providing a means for induction heating
   b) placing said anvil member in a heat sink configured and dimensioned to receive said anvil member such that a first part of the exterior surface of the anvil is in thermally conductive contact with said heat sink and a second part of the exterior surface of the anvil is exposed;
   c) positioning said heat sink in proximity to said inducting heating means such that the delimited portion of the second part of the exterior surface of the anvil is within heating range of said induction heating means;
   d) operating said induction heating means such that said delimited portion of the anvil member is heated to an annealing temperature; and
   e) terminating the heating operation when said annealing temperature is reached.

* * * * *